United States Patent [19]

Franzen

[11] Patent Number: 5,458,564
[45] Date of Patent: Oct. 17, 1995

[54] WRIST BRACE

[76] Inventor: Paul W. Franzen, 550 Ridge Pike, Lafayette Hill, Pa. 19444

[21] Appl. No.: 156,073

[22] Filed: Nov. 23, 1993

[51] Int. Cl.⁶ .................................................. A61F 5/00
[52] U.S. Cl. .............................. 602/21; 2/16; 128/878
[58] Field of Search ................................ 602/5, 20–22; 601/23, 33, 40; 128/877–880; 2/16, 910, 161.1

[56] References Cited

U.S. PATENT DOCUMENTS

| | | |
|---|---|---|
| 2,287,821 | 6/1942 | O'Donovan . |
| 3,327,703 | 6/1967 | Gamm . |
| 3,855,633 | 12/1974 | Rhee .................................... 2/161.1 X |
| 4,062,073 | 12/1977 | Rhee ............................................ 2/16 |
| 4,441,490 | 4/1984 | Nirschl . |
| 4,584,993 | 4/1986 | Nelson . |
| 4,677,971 | 7/1987 | Lindemann ................................ 602/21 |
| 4,765,319 | 8/1988 | Finnieston et al. ....................... 602/21 |
| 4,807,302 | 2/1989 | Cannella ..................................... 2/16 |
| 4,850,341 | 7/1989 | Fabry et al. . |
| 4,854,309 | 8/1989 | Elsey . |
| 4,883,073 | 11/1989 | Aziz . |
| 4,899,763 | 2/1990 | Sebastian et al. . |
| 4,941,460 | 7/1990 | Working . |
| 4,977,890 | 12/1990 | Mann ........................................ 602/21 |
| 5,002,044 | 3/1991 | Carter .................................... 602/21 X |
| 5,014,689 | 5/1991 | Meunchen et al. . |
| 5,058,576 | 10/1991 | Grim et al. ............................... 602/21 |
| 5,113,849 | 5/1992 | Kuiken et al. ........................ 602/21 X |

Primary Examiner—Linda C. M. Dvorak
Attorney, Agent, or Firm—John P. Blasko

[57] ABSTRACT

A wrist brace to prevent injury to persons such as concrete finishers who repetitively use their arms to support themselves or exert pressure against an object is disclosed. The wrist brace has a support element for maintaining the wearer's hand in a clenched fist configuration and a planar alignment of the hand, wrist and forearm. The support element is secured to the dorsal side of the wearer's arm by straps. The brace has a hand strap for securing the support element against the hand and maintaining the hand in a clenched fist during use of the brace. The support element also has cushioning such as foamed polyurethane adjacent to the wearer's arm. The support element may also have a hinge near the forearm to permit wrist and hand portions of the support element to be rotated thereby permitting the brace to be slidably retracted along the arm when the brace is not in use. This obviates the need to remove the brace entirely from the arm. Optionally, a protective guard may be positioned on the hand portion of the support element where contact with the object such as a floor will be made.

5 Claims, 1 Drawing Sheet

WRIST BRACE

FIELD OF THE INVENTION

The invention relates to a wrist brace for cushioning a wearer's forearm and bracing the wearer's wrist when the wearer is using the arm to support himself or exert pressure with the arm.

BACKGROUND OF THE INVENTION

From time to time, people use their hands and arms to support the weight of their body or exert other pressure against an object. For example, concrete finishers may typically use one arm to support themselves while using the other arm to trowel or finish the concrete they are working on. Problems arise when a person repetitively exerts pressure or exerts pressure against an object with excessive force in an open-handed or open palm manner. The stresses caused by exerting pressure in this manner may damage the ligaments, tendons, muscles and nerves of the wrist, hand and forearm. Therefore, it would be desirable to provide a device that maintains the hand, wrist and forearm in an alignment which reduces the risk of injury to a person exerting pressure against an object. It would also be desirable to provide a device that is easily removable when the wearer is not leaning on or exerting pressure with his arm. When reference is made to the following description taken in conjunction with the accompanying drawing, it will become apparent how the wrist brace of the present invention achieves these objects and additional advantages.

SUMMARY OF THE INVENTION

The present invention relates to a wrist brace for preventing injury to persons such as concrete finishers who repetitively use their arms to support themselves or exert pressure against a movable or immovable object. The wrist brace has a support element for maintaining the wearer's hand in a clenched fist configuration and a planar alignment of the hand, wrist and forearm. The support element is secured to the dorsal side of the wearer's arm by fastening means, preferably straps. The brace has a hand strap for securing the support element against the hand and maintaining the hand in a clenched fist during use of the brace. The support element also has a cushioning means such as foamed polyurethane adjacent to the wearer's arm. The support element may also have a hinge means near the forearm to permit wrist and hand portions of the support element to be rotated thereby permitting the brace to be slidably retracted along the arm when the brace is not in use. This obviates the need to remove the brace entirely from the arm. Optionally, a protective guard may be positioned on the hand portion of the support element where contact with the object such as a floor will be made.

The wrist brace of the present invention comprises a support element adapted to be secured to the dorsal side of the wearer's forearm, wrist and hand and to maintain the metacarpal bones of the hand in a generally planar relation to the ulna and radius of the forearm. The support element has a hand portion generally perpendicular to a wrist portion to maintain the wearer's hand in a clenched fist configuration, and it has a cushioning means along the interior side of the support element adjacent to the wearer. The cushioning means may be an integrally molded foam plastic, such as polyurethane. The wrist brace also comprises a strap means for securing the support element to the wearer's hand located so as to pass across the palm and secure the hand to the brace and a fastening means for securing the support element to the wearer's forearm. The support element may further comprise a hinge means near the forearm for permitting the wrist and hand portions to be rotated and the wrist brace to be slidably, longitudinally retracted along the wearer's arm thereby permitting use of the wearer's hand without removing the brace from the wearer's arm.

DETAILED DESCRIPTION OF THE PREFERRED EMBODIMENT

Figure 1:
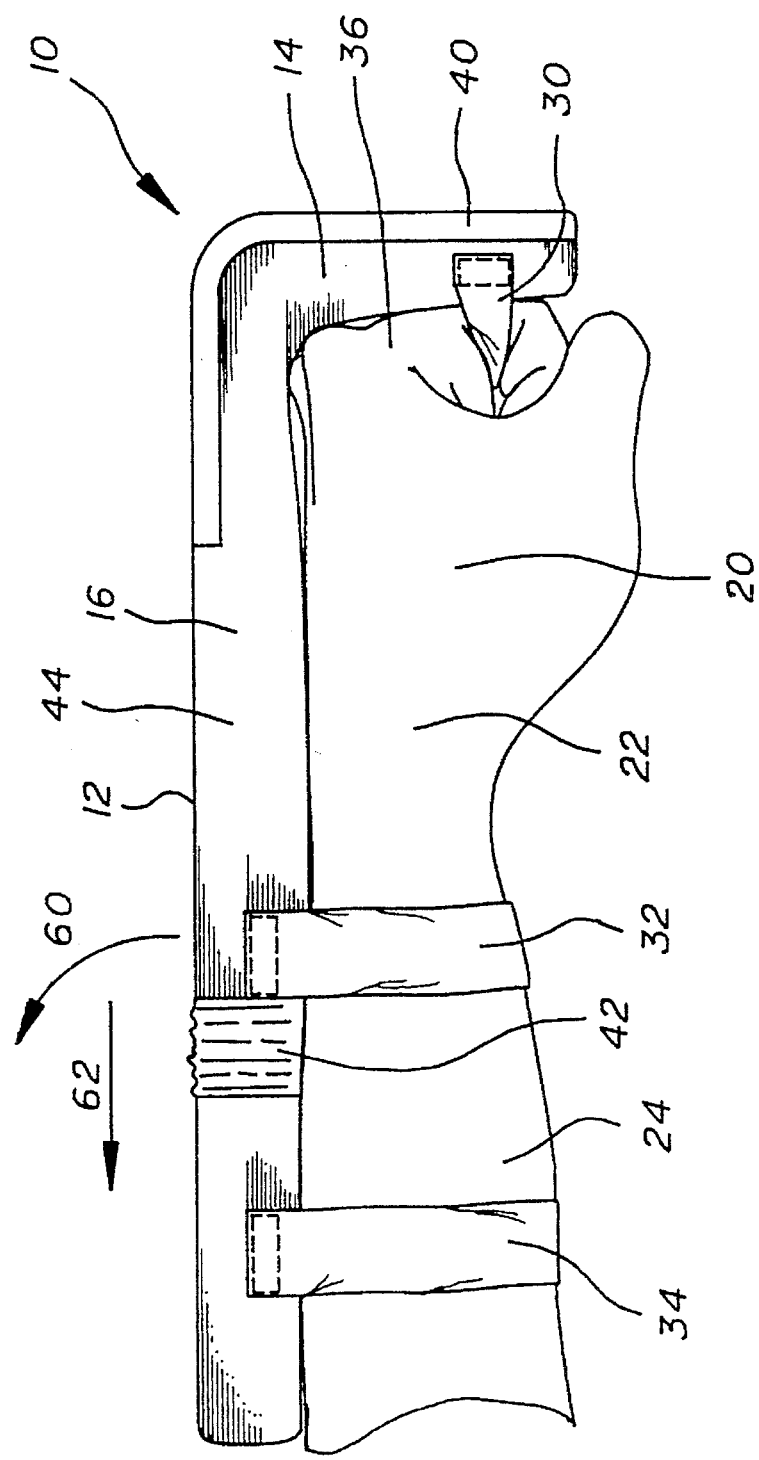
FIG. 1 depicts a radial view of the wrist brace in use on the wearer's forearm, wrist and hand. The support element may also have a rigid protective guard means located on the exterior of the hand portion of the support element.

In describing a preferred embodiment of the invention illustrated in the drawings, specific terminology will be used for the sake of clarity. However, the invention is not intended to be limited to the specific terms so selected, and it is to be understood that each specific term includes all technical equivalents which operate in a similar manner to accomplish a similar purpose.

With reference to FIG. 1, a brace 10 according to the present invention worn on the left forearm 24, wrist 22 and hand 20 of a wearer is shown.

Wrist brace 10 comprises support element 12 which extends from a position on forearm 24 below the wearer's elbow along the dorsal side of the arm to the distal end of the first row of phalanges. Support element 12 is generally planar along it length and has a width approximately equal to the width of the hand. Support element 12 is comprised of hand portion 14 which covers the area of the phalanges and wrist portion 16 adjacent to the metacarpals and wrist. Hand portion 14 is generally perpendicular to wrist portion 16. This configuration maintains the hand, wrist and forearm in the most stable alignment for exerting pressure along the contact surface of hand portion 14. The ulna, radius, carpus and metacarpus are aligned in a generally planar relation.

Support element 12 also comprises cushioning means 44 along the interior side of the brace adjacent to the wearer's arm. The cushioning means may be any suitable cushioning material such as foam plastic or the like such as are used in the manufacture of protective knee pads. A rigid foam plastic such as a closed cell polyurethane may be employed thereby combining the support and cushioning functions and obviating the need for additional support structure within the brace.

Wrist brace 10 is secured to the wearer by hand strap 30 and forearm fasteners 32 and 34. Hand strap 30 is preferably an elastic strap material integrally attached to the side edges of hand portion 14 of support element 12. Hand strap 30 passes over fingers 36 and the palm of the wearer. Its positioning aids in maintaining the wearer's hand in a clenched fist configuration. Forearm fasteners 32 and 34 may be elastic straps integrally attached to support element 12 or each fastener may be a pair of corresponding straps and tabs with, for example, releasable interlocking hook and loop fastener means such as are sold under the trademark Velcro.

In a preferred embodiment, wrist brace 10 comprises a rigid protective guard 40 positioned over the exterior surface of hand portion 14 where contact will be made with the object against which pressure will be exerted by the wearer.

The protective guard is useful for protecting the cushioning means from excessive wear and tear, and may be fabricated from any suitable material such as high density polyethylene or the like.

Support element 12 also comprises a hinge 42 located in the vicinity of forearm 24. Hand portion 14 and wrist portion 16 of support element 12 may be rotated at hinge 42 in the direction of arrow 60 to permit hand portion 14 to pass over the knuckles of hand 20 and wrist brace 10 to be slidably retracted along the arm in the direction of arrow 62 when the wrist brace is not in use. This permits the use of the wearer's hand without completely removing the wrist brace from the wearer's arm.

Although this invention has been illustrated by reference to specific embodiments, it will be apparent to those skilled in the art that various changes and modifications may be made which clearly fall within the scope of the invention. The invention is intended to be protected broadly within the spirit and scope of the appended claims.

What is claimed is:

1. A wrist brace comprising:

a support element adapted to be secured to the dorsal side of the wearer's forearm, wrist and hand and to maintain the metacarpal bones of the hand in a generally planar relation to the ulna and radius of the forearm, said support element having a hand portion generally perpendicular to a wrist portion to maintain the wearer's hand in a clenched fist configuration, and having a cushioning means along the interior side of the support element adjacent to the wearer, wherein the wrist portion comprises a first wrist portion and a second wrist portion, and the support element comprises a hinge means located between the first and second wrist portions for permitting the first wrist portion and the hand portion to be rotated with respect to the second wrist portion;

a strap means for securing the support element to the wearer's hand located so as to pass across the palm and secure the hand to the brace;

a fastening means for securing the support element to the wearer's forearm.

2. A wrist brace according to claim 1, wherein the cushioning means comprises an integrally molded foam plastic.

3. A wrist brace according to claim 2, wherein the plastic is a polyurethane.

4. A wrist brace according to claim 1, wherein the support element further comprises a rigid protective guard means located on the exterior of the hand portion of the support element.

5. A wrist brace according to claim 2, wherein the support element further comprises a rigid protective guard means located on the exterior of the hand portion of the support element.

* * * * *